United States Patent [19]

McKelvey

[11] 4,397,395

[45] Aug. 9, 1983

[54] DENTAL BURR HOLDER

[75] Inventor: Thomas H. McKelvey, Macon, Ga.

[73] Assignee: The Inventors Collaborative, Inc., Macon, Ga.

[21] Appl. No.: 114,337

[22] Filed: Jan. 23, 1980

[51] Int. Cl.³ .............................................. A47F 7/00
[52] U.S. Cl. ................................. 211/60 T; 206/369; 433/79
[58] Field of Search ................... 211/69, 60 T, 60 R, 211/69.5, 13; 206/368, 369, 379; D24/10, 31; 433/77, 79

[56] References Cited

U.S. PATENT DOCUMENTS

| | | | |
|---|---|---|---|
| 222,107 | 11/1879 | Waters | 211/69 X |
| D. 222,791 | 12/1971 | Costello | D83/1 |
| D. 242,545 | 11/1976 | Perfect | D24/1 R |
| 691,695 | 1/1902 | Aderer | 206/369 |
| 1,104,650 | 7/1914 | Fries | |
| 1,121,934 | 12/1914 | Miller | 211/69 |
| 1,357,063 | 10/1920 | Korb | 211/69 |
| 1,519,614 | 12/1924 | Heck | 211/69 |
| 2,842,260 | 7/1958 | Molitor | 211/69 X |
| 2,940,809 | 6/1960 | Herzog | 211/69 X |
| 2,971,637 | 2/1961 | Simons | 206/369 |
| 3,102,637 | 9/1963 | Scholl, Sr. | 211/69 |
| 3,145,841 | 8/1964 | McGuire | 206/72 |
| 3,236,366 | 2/1966 | Broda et al. | 206/17 |
| 3,270,416 | 9/1966 | Massa | 32/22 |
| 4,032,008 | 6/1977 | Vecchiarilli | 206/379 |

OTHER PUBLICATIONS

1976 Catalog, Published by Silverman's Appollo Road, Plymouth Meeting, Pa., 19462, pp. 56 & 176.

*Primary Examiner*—Francis K. Zugel
*Assistant Examiner*—Robert W. Gibson, Jr.
*Attorney, Agent, or Firm*—Roylance, Abrams, Berdo & Farley

[57] ABSTRACT

A dental burr holder comprising a holder body adapted to rest on a support and having a smooth, upper surface interrupted by a plurality of upwardly opening burr receiving apertures, and a member projecting generally upwardly from the holder body and having a smooth front surface which faces across the upper surface of the holder body. These two surfaces form a background which color contrasts with the burrs and against which the burrs are viewed. The background is continuously color contrasting and is substantially visually uninterrupted except for the burr receiving apertures. This structure allows quick and accurate selection of the desired burr silhouetted against the contrasting background, and also makes the problem of detecting damaged or imperfect burrs easier. With dark colored burrs, a white background is preferred.

29 Claims, 20 Drawing Figures

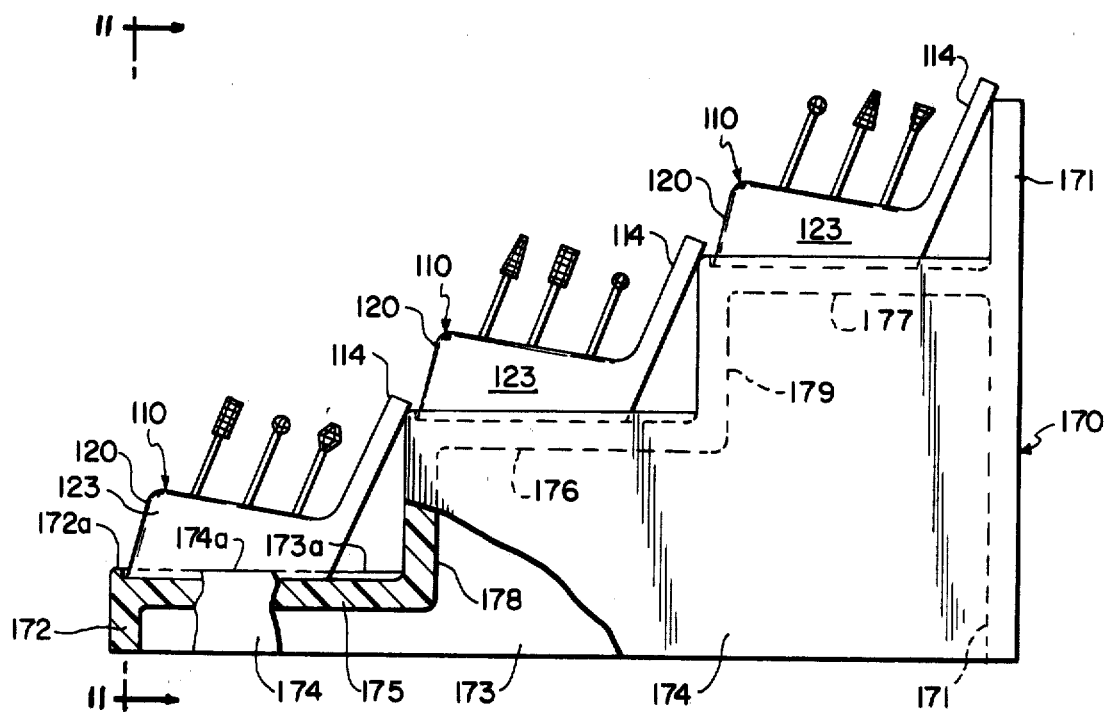
FIG. 10
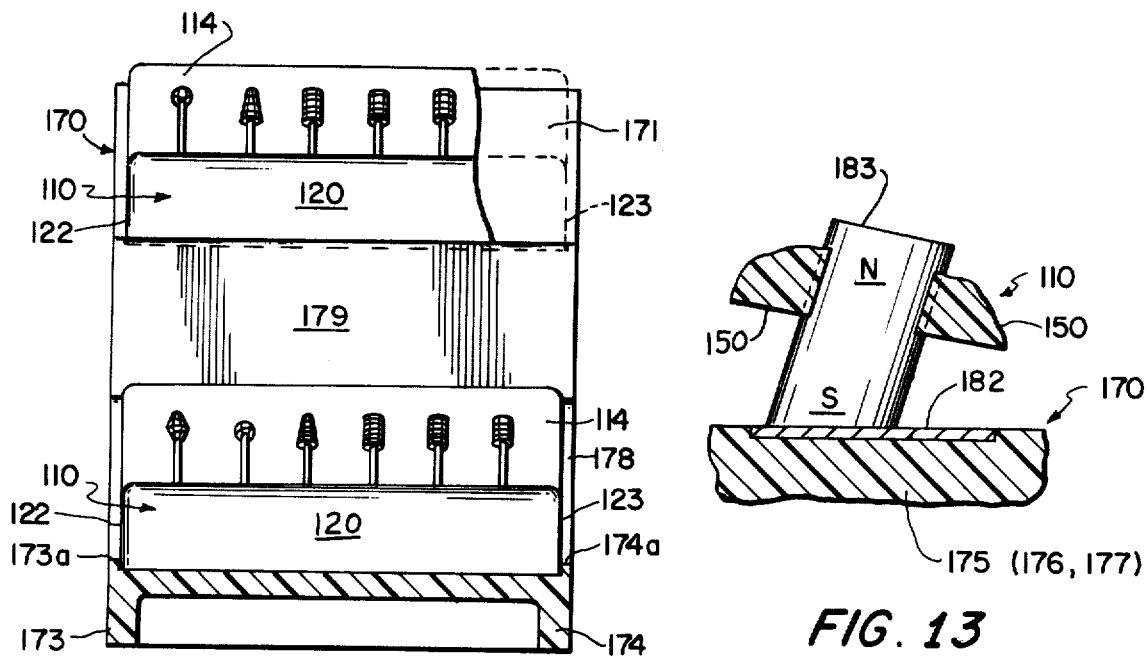
FIG. 11
FIG. 13

DENTAL BURR HOLDER

FIELD OF THE INVENTION

The invention relates to a holder for small dental tools, typically dental burrs. The holder supports a plurality of the burrs in such manner that the dentist or dental assistant can more quickly and accurately select and pick up the desired burr and can observe damaged or imperfect burrs.

BACKGROUND AND PRIOR ART

Dental burr holders or supports are well known in the art, and usually comprise a horizontal supporting body having a plurality of vertically oriented bores, each bore receiving the shank of a burr. These supports are usually placed on the dentist's work tray adjacent the dental chair or on a separate shelf or tray within reach of the dentist or the dental assistant. These supports retain the numerous burrs utilized during the various drilling operations commonly performed by the dentist.

Dental burrs are typically of hardened metal such as stainless steel, the burr being about 2.5 cm. long and about 0.25 cm. in diameter and fixed to a shank to fit the dentist's handpiece. The tips of such dental burrs have different configurations, depending upon their use. Such tip shapes include inverted cones, balls, round-edge or square-edge wheels, flat-end or round-end tapers, flames and cavicuts. In each case, such dental burrs are relatively small and to a degree damageable. Because the different types of burrs are distinguishable only by observing the tip configuration, it is very easy to confuse them and difficult to observe when a burr has been damaged. And it is correspondingly easy for the dentist or dental assistant to pick up the wrong burr or a damaged burr. Such a mistake is costly to the dentist and the patient for at least three reasons. First, the mistake wastes time when time is of the essence, i.e., when the patient is in the dentist's chair and drilling is being performed, the patient then commonly being in pain and usually having nerve ends of the tooth exposed. Second, use of an incorrectly chosen burr can damage the patient's tooth and nerve. Third, use of a burr with unobserved broken or damaged cutting blades increases the patient's discomfort and sometimes causes the tooth to develop craze lines.

Thus, an effective dental burr holder should not only adequately support the burrs but also display them in such fashion that the dentist or dental assistant can make quick, easy and accurate selection and have a maximum opportunity to observe whether the burr is damaged or imperfect. Unfortunately, prior-art holders promote neither speed nor accuracy of burr selection, nor do they aid in detecting damaged or imperfect burrs.

Such prior-art dental burr holders include those disclosed in U.S. Pat. Nos. 1,104,650, issued July 2, 1914, to Fries; 3,102,637, issued Sept. 3, 1963, to Scholl; 3,270,416, issued Sept. 6, 1966, to Nassa; and U.S. Pat. No. Des. 242,545, issued Nov. 30, 1976, to Perfect; and the 1976 catalog published by Silverman, Apollo Rd., Plymouth Meeting, Pa. 19462. Each of these prior-art devices discloses a horizontal support having a plurality of vertically oriented bores for receiving the shank of a dental burr.

In addition, U.S. Pat. Nos. 3,145,841, issued Aug. 25, 1964, to McGuire and U.S. Pat. No. Des. 222,791, issued Dec. 28, 1971, to Costello disclose hospital trays having a plurality of vertically oriented bores for receiving things such as small cups of medicine. Finally, U.S. Pat. No. 3,236,366, issued Feb. 22, 1966, to Broda discloses a carrying case for drill bits used for drilling materials such as wood and metal.

Unfortunately, none of these prior art devices provides an environment in which the small, lightweight and visually confusing dental burrs can be quickly, easily and accurately selected by the dentist or dental assistant. In fact, prior-art workers seem not even to have recognized the need for such advantages or the problem of visually distinguishing the burrs in the holder. As recently as January, 1980, a major supplier to the dental trade, recognizing that the holders should be sterilizable by autoclaving, proposed to offer a holder formed of stainless steel and thus presenting a background surface against which the stainless steel burrs would be difficult even to see, let alone distinguish by type.

SUMMARY OF THE INVENTION

The invention is based on recognition of the reason for the problem in the art and a solution to that problem. Specifically, the deficiency of the prior art dental burr holders, which results in the problem of inaccurate and slow selection of the desired dental burr, is that prior-art burr holders support the burrs in a fashion making them difficult to see and distinguish one from another. This is because the background against which the burrs are viewed is visually confusing, providing little, if any, consistent color contrast to the burrs and being visually interrupted by irregular shapes, textures, and shadows. Thus, the distinguishing silhouette of the burrs' tips are difficult to see and recognize.

In particular, some of the prior art devices have no specific background structure, so that the background against which the dental burr is viewed is any random surface or object adjacent the dental burr holder. Thus, since most dental burrs are formed from dark, hardened metal, such as steel, they are very difficult to identify if there are other metallic articles lying adjacent the burr support, which is very typical on a dentist's tray where other metallic objects such as mirrors, tweezers, and various clamps are common. In those prior-art devices providing a background, the background fails to color contrast with the dental burrs, thus obscuring the distinguishing silhouette of the burrs.

Accordingly, it is a primary object of the present invention to provide an improved dental burr holder having a color contrasting and substantially visually uninterrupted background for the supported dental burrs allowing for a quick and precise selection of the desired burr by making the distinguishing silhouette of the burrs clearly observable.

Another object of the invention is to provide such a dental burr holder which is cheap to manufacture and easy to use.

A further object is to devise a burr holder which, though compact and of light weight, is capable of being sterilized by autoclaving.

Yet another object is to provide such a device which is of such configuration that a plurality of the devices can be supported in related positions with the burrs of each holder being readily and clearly observable.

The foregoing objects are attained by providing a dental burr holder comprising a body adapted to rest on a support and having a smooth upper surface interupted only by a plurality of upwardly opening burr receiving apertures; and a member projecting generally upwardly from the holder body and having a smooth front surface which faces across the upper surface of the holder body, the upper surface and the front surface forming a background which color contrasts with the burrs to be received in the holder and against which these burrs are viewed, the background being continuously color contrasting and substantially visually uninterrupted except for the burr receiving apertures to allow quick and accurate selection of the desired burrs supported in the holder and silhouetted against the contrasting background.

As used in this specification, the phrase "color contrast" means a diversity of adjacent elements in color. The phrase "substantially visually uninterrupted" means, when viewed by the human eye, the background has a uniform, continuous surface of a smooth, regular texture with a lack of shadow-forming irregularities, there being no incongruities except for the transition from the upper surface to the side surface of the holder. Finally, as used in this specification, the phrase "continuously color contrasting" means that the color of the background of the holder varies only slightly in shade throughout its entire extent and the overall background color contrasts with the color of the dental burrs.

Other objects, advantages and salient features of the invention will become apparent from the following detailed description which, taken in conjunction with the annexed drawings, discloses particularly advantageous embodiments of the invention.

DRAWINGS

Referring now to the drawings which form a part of this original disclosure:

FIG. 10 is an end elevational view showing three of the burr holders of FIGS. 6-8 combined with a support, a portion of the support being broken away for clarity of illustration;

FIG. 11 is a front elevational view of the combination shown in FIG. 10 but with one burr holder removed and portions broken away for clarity.

FIG. 13 is a fragmentary vertical sectional view showing another releasable securing means;

DETAILED DESCRIPTION OF THE INVENTION

Figure 1:
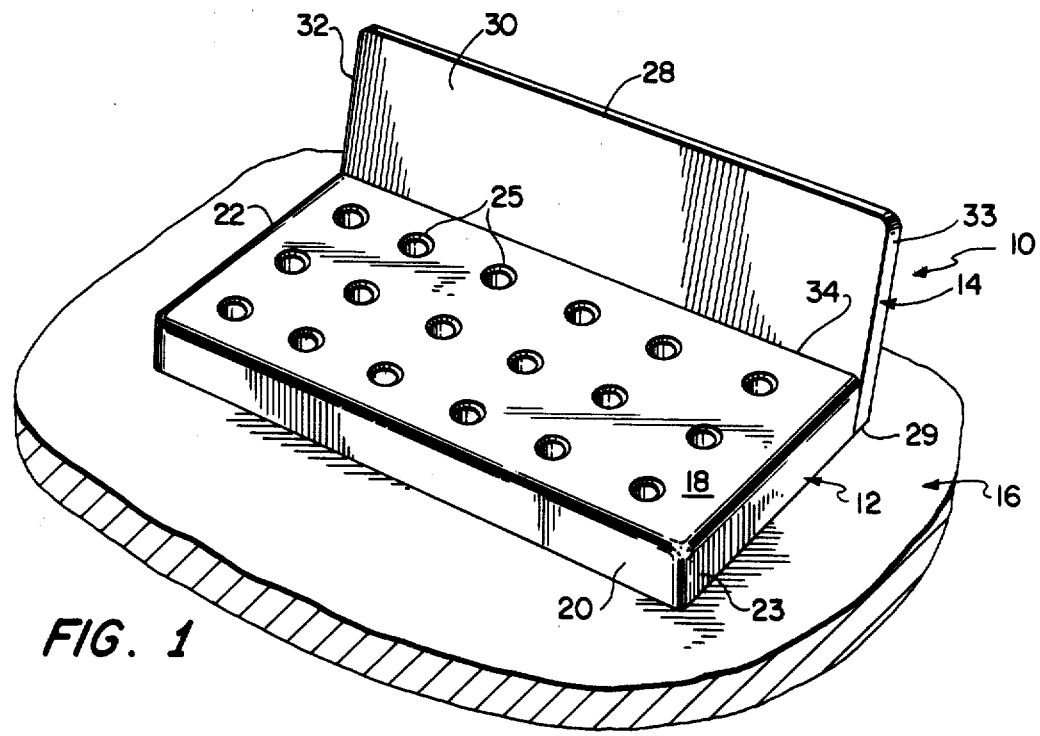
FIG. 1 is a frontal perspective view of a dental burr holder according to the invention, the holder being shown located on a support.
Figure 2:
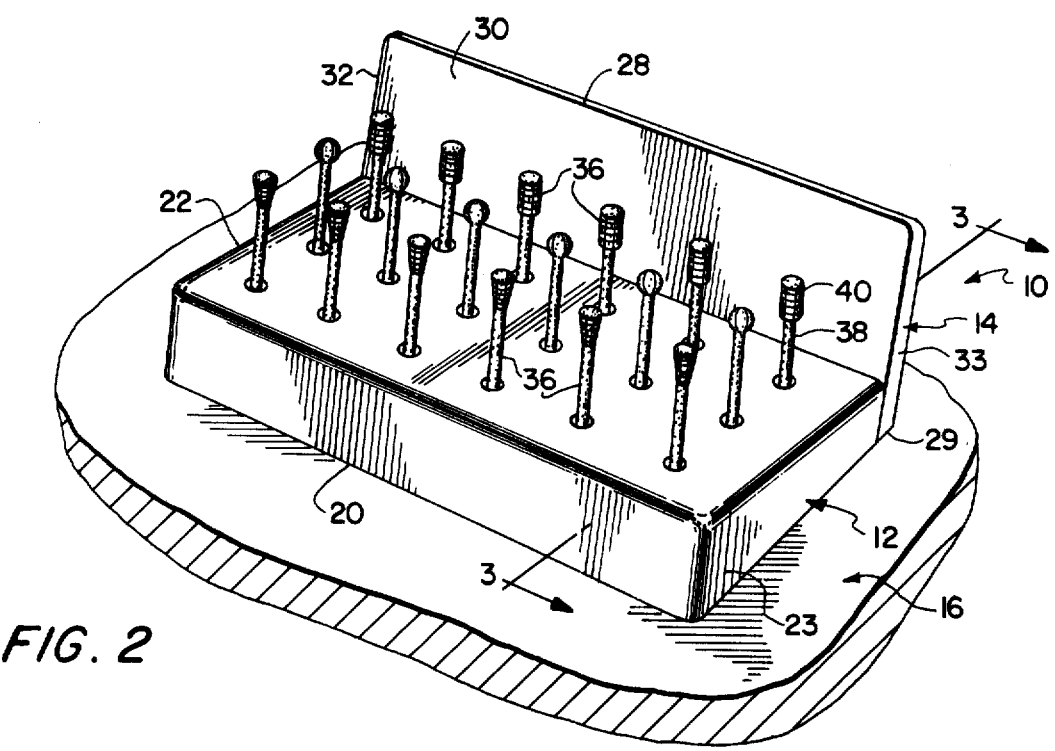
FIG. 2 is a perspective view of the holder of FIG. 1 with a plurality of dental burrs supported therein.
Figure 3:
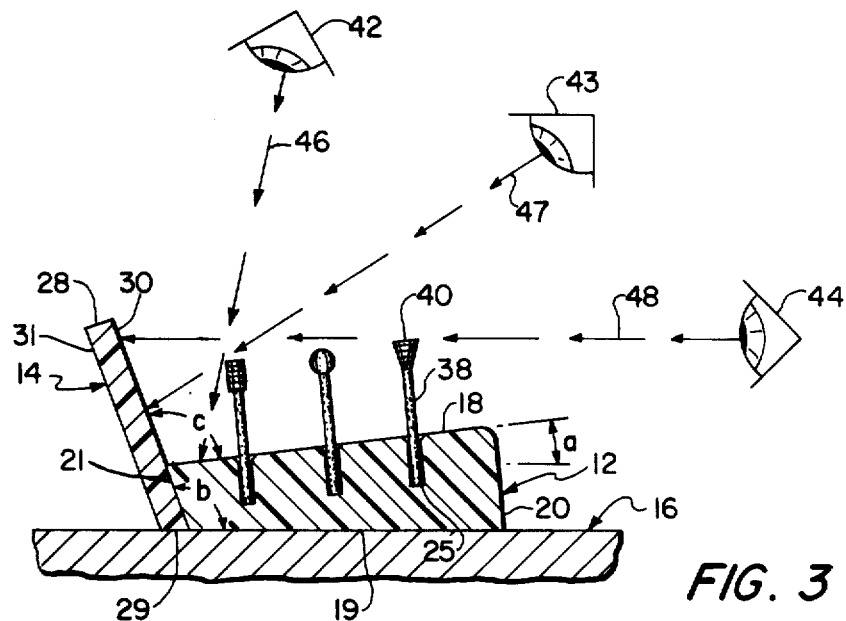
FIG. 3 is a sectional view taken generally on line 3—3, FIG. 2, showing a plurality of dental burrs supported in the holder and illustrating the line of sight by a human eye in three different positions.
Figure 4:
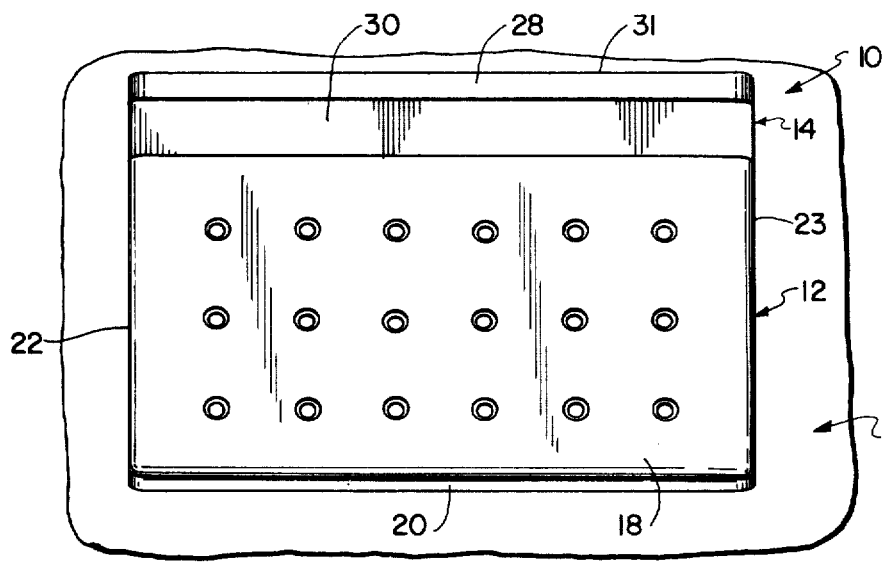
FIG. 4 is a top plan view of the holder of FIG. 1.

Referring now to FIGS. 1, 2 and 4, the dental burr holder 10 in accordance with one embodiment of the invention is formed of polymeric material and comprises a holder body 12 and a member 14 projecting generally upwardly from the holder body. As seen in FIGS. 1-5, holder 10 is adapted to be supported on a flat support surface 16, which can be a tray or shelf located in the dentist's working area.

Body 12 is a six-sided parallelepiped having smooth, planar surfaces including a top surface 18, a bottom surface 19, a front surface 20, a rear surface 21, a left end or side surface 22 and a right side surface 23. Front surface 20 is substantially perpendicular to the flat support 16 and top surface 18 is at a small acute angle "a" of about 5° to about 10° to support 16. The rear surface 21 is inclined rearwardly at an angle "b" of about 95° to about 105° to the support 16. The top, bottom, front and rear surfaces are rectangular.

A plurality of burr-receiving apertures 25 are formed as upwardly opening bores in the holder body 12. In this embodiment, apertures 25 are arranged in three rows of four apertures, though any desired number and spatial arrangement consistent with the size of the holder body can be employed. Advantageously, as seen in FIG. 3, bores 25 extend at, or substantially at, right angles to top surface 18 and are flared outwardly at their upper ends to provide short frustoconical entrance surfaces 25a. Bores 25 extend downwardly below the top surface 18 a sufficient distance to accommodate a substantial portion of the lengths of the shanks of the burrs, but do not extend completely through the holder body 12.

Member 14 projects generally upwardly from the holder body and is rigidly secured, as by adhesive, to the rear surface 21, or is made integral with the body. Member 14 is a six-sided parallelepiped, all six sides being smooth and planar. These sides include a top surface 28, a bottom surface 29, a front surface 30, a rear surface 31, a left end surface 32 and a right end surface 33. Each of these surfaces is rectangular except for the two end surfaces. Bottom surfaces 29 and 19 of body 12 and member 14 are coplanar.

As best seen in FIG. 1, front surface 30 of member 14 extends completely across the width of the top surface 18 of holder body 12 with only a very light line 34 being visible at the transition between surfaces 18 and 30. This line 34 is the result of forming the member 14 and holder body 12 of separate parts and can be eliminated if these two elements are integrally formed, which they can be as desired. In all events, while line 34 is visible, it does not interfere with the substantially visually uninterrupted continuum formed by the top surface 18 and front surface 30, as described hereinafter in further detail.

Advantageously, front surface 30 of member 14 extends upwardly above the top surface 18 a distance greater than the length of the exposed portions of the burrs received in the burr receiving apertures 25, as seen in FIG. 3. The angle "c" between the front surface 30 and the top surface 18 is from about 95° to about 105°.

Advantageously, body 12 and member 14 are formed from polymeric material having the same white color. Alternatively, the holder body 12 has a white color and the upwardly projecting member 14 has a somewhat darker off-white color. In all events, the upper or top surface 18 of the holder body 12 and the front surface 30 of the upwardly projecting member 14 form a background which color contrasts with the color of the burrs adapted to be received in the holder and against which these burrs are viewed, as seen in FIGS. 2 and 3. This background is continuously color contrasting and substantially visually uninterrupted except for the burr receiving apertures to allow quick and accurate selection of the desired burrs in the holder and silhouetted against this contrasting background. As used herein, the colors white and off-white are meant to mean that the upper surface 18 and the front surface 30 have reflectivity characteristics so as to reflect substantially all portions of the spectrum in the range of from about 400 to about 800 millimicrons at intensities which do not vary by more than 10%. In all events, the crux of the invention is to provide a continuous contrast in color between the holder 10 and the burrs supported therein and a substantially visually uninterrupted background. It is also helpful to have a contrast in texture provided by making the surfaces 18 and 30 smooth.

As seen in FIGS. 2 and 3, the burrs 36 received in the burr receiving apertures 25 have a main shank portion 38, FIG. 2, and a tip portion 40. As seen in FIG. 3, the shank portion 38 is received in the aperture, rests on the bottom thereof and extends upwardly therefrom for a distance such that tip portion 40 is located above surface 30 in clear view. These tip portions come in many different configurations, the ones shown in FIGS. 2 and 3 including three of the common shapes. Those shown are the square-edge wheel type, in the row closest to the upwardly projecting member 14; the ball type in the middle row; and the inverted cone type located in the row closest to surface 20. In addition, there are the round-edge wheel type, the flat end taper type, the round-end taper type, the flame type and the cavicut type, and it will be apparent that, for practical purposes, the various types of burrs are identifiable at the time of selection only by observing the tip portion silhouettes.

Typically, dental burrs are formed from hardened metal, such as steel, and have a dark grey or light metallic blue color, as represented by the shading shown in FIGS. 2 and 3.

Once the burrs 36 are received in the holder 10 as seen in FIGS. 2 and 3, they contrast starkly with the background formed from the upper or top surface 18 of the holder body 12 and the front surface 30 of the upwardly projecting member 14 which provides continuous color contrast and a substantially visually uninterrupted background. Thus, when the dentist or the dental assistant looks toward the holder 10 to select the desired burr 36, that burr which is desired can be very accurately and quickly selected because of the clear contrast of the burrs silhouetted against the contrasting, uninterrupted background. This is diagramatically illustrated in FIG. 3 in which the three human eyes 42, 43 and 44 are shown viewing the holder 10 from three different lines of sight 46, 47 and 48, respectively. As will be apparent from FIG. 3, from any of these positions, the burrs 36 are consistently viewed against the contrasting background of the holder 10, thereby providing the dentist or the dental assistant an opportunity to observe the burrs' distinguishing silhouettes and quickly and accurately select the desired burr.

Considering FIGS. 2 and 3, it will be apparent that the positions of the burrs relative to the holder, and the presence of a continuously contrasting and substantially visually uninterrupted background surface afforded by members 12 and 14, afford the dentist or dental assistant a maximum opportunity to see the tips of the burrs with such clarity and in such detail that it can be observed whether the particular burr to be selected has been damaged or is imperfect.

Figure 5:
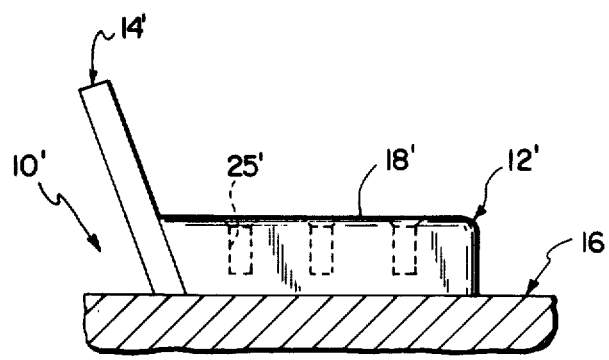
FIG. 5 is an end elevational view of a modified form of the holder of FIG. 1.

As seen in FIG. 5, an alternative embodiment of the holder 10' can comprise a holder body 12' which has a top or upper surface 18' parallel to the flat support 16. In this case, the burr receiving apertures 25' have their longitudinal axes perpendicular to the support 16 as well as to the upper surface 18'. In addition, the upwardly projecting member 14' is at an angle of about 100° relative to surface 18'.

Figure 6:
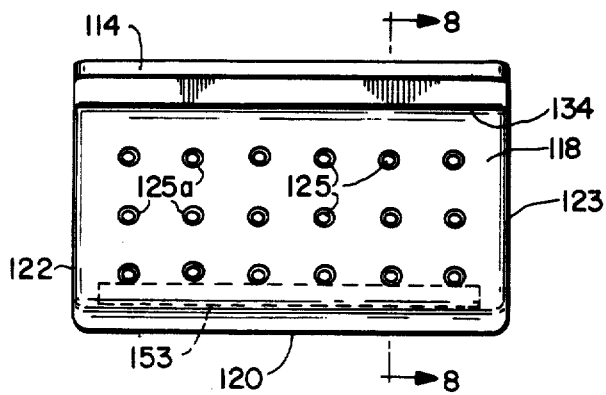
FIGS. 6 and 7 are top plan and front elevational views, respectively, of a burr holder according to another embodiment.
Figure 8:
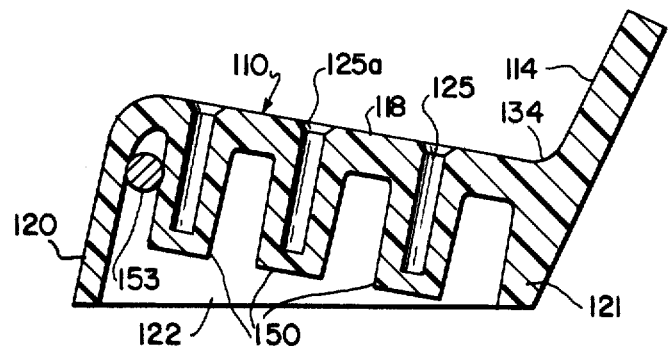
FIG. 8 is a sectional view taken generally on line 8—8, FIG. 6.
Figure 7:
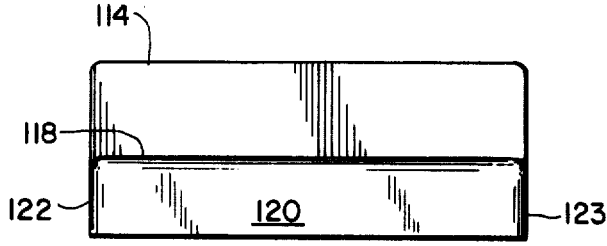

FIGS. 6–8 illustrate an embodiment of the holder adapted for low cost volume production. Here, body portion 110 and upwardly projecting portion 114 are formed integrally, as by injection molding, from white or milky white polypropylene. While portion 114 is solid, body portion 110 is hollow and has a top wall 118, front wall 120 and end walls 122 and 123, the back wall 121 being an integral continuation of portion 114. The bottom edges of walls 120–123 are coplanar. The flat upper surface of wall 11 is inclined rearwardly toward the common plane of the bottom edges of walls 120–123 at an angle of from about 5° to about 10°. The angle between the flat front face of portion 114 and the common plane of the bottom edges of walls 120–123 is from about 95° about 105°. The junction between the front face of portion 114 and the upper surface of top wall 118 is filleted at 134 so that no clearly visible junction line is present to interrupt the white background surface presented by portion 114 and wall 118. To provide for bores 125, top wall 118 has a plurality of dependent bosses 150 which project into the cavity defined by walls 118 and 120–123 and at right angles to the flat top surface of wall 118, both the bosses 150 and bores being of circular transverse cross section. Short downwardly tapering frustoconical entrance surfaces 125a are provided at the mouths of bores 125.

Figure 8A:
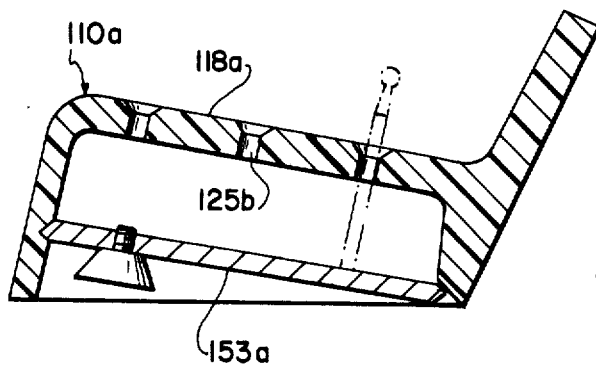
FIG. 8A is a view similar to FIG. 8 showing a modification of the device of FIGS. 6-8.

As shown in FIG. 6, the holder has eighteen bores 125 arranged in three parallel rows of six, the three rows being parallel to portion 114 and front wall 120. Thus, as seen by comparing FIGS. 6 and 8, a straight series of six of the bosses 150 is spaced rearwardly from front wall 120. The bosses of that series are provided with axially aligned notches at 151, FIG. 8. The inner face of wall 120 is provided with a groove at 152, FIG. 8, and a straight stainless steel rod 153, which is slightly shorter than the space between end walls 122 and 123, is wedged between front wall 120 and the adjacent line of eight bosses 150. The purpose of rod 153 is to provide added weight to assure that the holder will remain stable when positioned on a tray or other horizontal support. Alternatively, bosses 150 can be omitted, as in FIG. 8A, so that bores 125b open through top wall 118a into the cavity. The metal weight member is then made as a flat plate 153a engaged in inwardly opening grooves in the dependent walls of body 110a so that the inserted ends of the burr shanks rest on plate 153a as shown.

Figure 9:
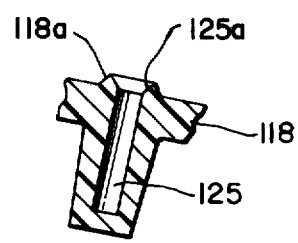
FIG. 9 is a fragmentary sectional view showing another modification of the device of FIGS. 6-8.

Bores 125 are small, being only slightly larger in diameter than the shanks of the dental burrs to be received by the bore. Typical bore diameters are in the range of 0.06–0.1 inch. Since the shanks of the burrs tend to fill the bores, the bores do not significantly visually interrupt the white background surface presented by top wall 118. The short frustoconical surfaces 125a are correspondingly small, and with body 110 molded from white or milky white polymeric material, the difference between surfaces 125a and the main flat upper surface of wall 118 is hardly discernable by visual inspection. Yet surfaces 125a perform as guide surfaces, simplifying the task of inserting the shanks of the dental burrs into bores 125. If desired, as seen in FIG. 9, the upper ends of bores 125 can all lie in the plane of the flat upper surface of wall 118, and the short frustoconical guide surfaces 125a can be formed in bosses defined by the guide surfaces and an outer frustoconical surface 118a.

As shown in FIGS. 10 and 11, a plurality of the holders 110 can be combined with a support 170 so as to present the holders in staircase fashion. Support 170 is a hollow integral piece produced, for example, by injection molding from the same white or milky white polypropylene used for holders 110. Support 170 comprises an upright rear wall 171, a vertically short upright front wall 172, and end walls 173 and 174, the lower edges of walls 171–174 lying in a common plane which is horizontal when the support is in its normal position. The top wall of support 170 is of staircase configuration including three horizontal portions 175–177 interconnected by upright wall portions 178, 179. In plan form, each horizontal portion 175–176 is slightly larger than the plan form of one of the holders 110 and the upper surfaces of the portions 175–177 are each formed to provide an upwardly opening recess to accommodate the body 112 of one of the holders 110. Thus, horizontal top wall portion 175 is recessed to provide an upwardly projecting front rib 172a, a left end rib 173a and a right end rib 174a, ribs 173a and 174a being so spaced that, when the holder 110 is placed in the recess, ribs 173a and 173b frictionally engage end walls 122 and 123, respectively, of the holder 110 to releasably retain the holder in the recess.

When the three holders 110 are in place on support 170, the rearwardly inclined upwardly projecting portion 114 of each holder 110 extends upwardly beyond the wall portions 178, 179, 171 of support 170 and, for the front two of the holders 110, overlaps the front face 120 of the next adjacent holder 110, as seen in FIG. 10. Portion 114 of the uppermost one of the holders 110 extends beyond the upper edge of rear wall 171 of the support. Hence, when viewed from the front, the combination of support 170 and the three holders 110 presents a continuous, visually uninterrupted white background made up by the surfaces of the three overlapping holders 110.

Figure 12:
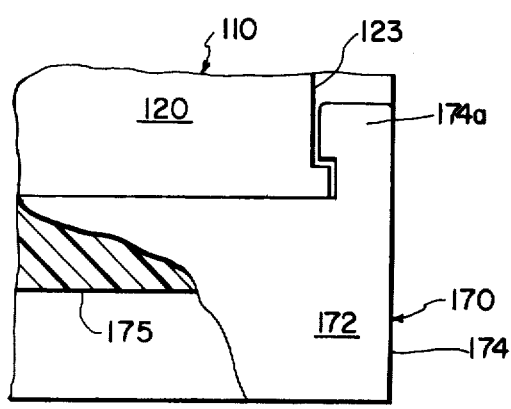
FIG. 12 is a fragmentary front elevational view showing one manner in which the burr holders can be releasably secured to the holder in the combination shown in FIGS. 10 and 11.

Other than the frictional engagement described above, various means can be employed to releasably secure holders 110 to support 170. Thus, as seen in FIG. 12, the three frontal ribs 172a, FIG. 10, can be eliminated, end ribs 173a and 174a can be provided with inwardly opening slots 180, and end walls 122, 123 of holders 110 can be provided with ribs, as at 181, FIG. 12, capable of slidably engaging in slots 180, slots 180 running from the front to the back of the respective top wall portions 175–177 and the ribs 181 running from the front edge to the back edge of the respective end walls 122, 123 of holder 110. With holders 110 and support 180 thus equipped, holders 110 can be moved horizontally into place in the respective wall portions 175–177 and can be withdrawn by horizontal movement forwardly and away from support 170. Alternatively, as shown in FIG. 13, each top wall portion 175–177 can be equipped with a small flat plate 182 of magnetic material, and a permanent magnet 183 can be retained between two of the bosses 150 of the holder 110, providing a magnetic latching action between the holder and support when the holder has been properly placed on the support.

Figure 15:
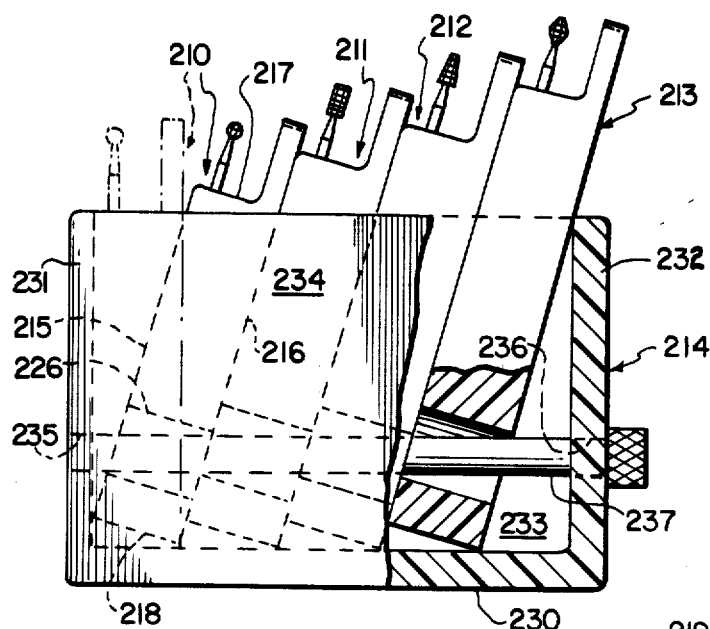
FIGS. 15 and 16 are, respectively, end and front elevational views of a plurality of the burr holders of FIG. 13 combined with a support, portions of the support being broken away.
Figure 14:
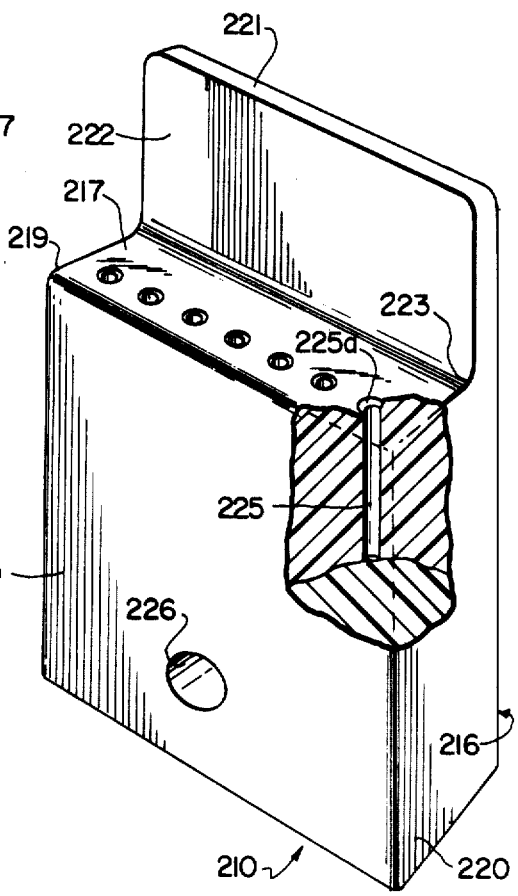
FIG. 14 is a perspective view of a burr holder according to another embodiment of the invention, a portion of the holder being broken away for clarity of illustration.
Figure 16:
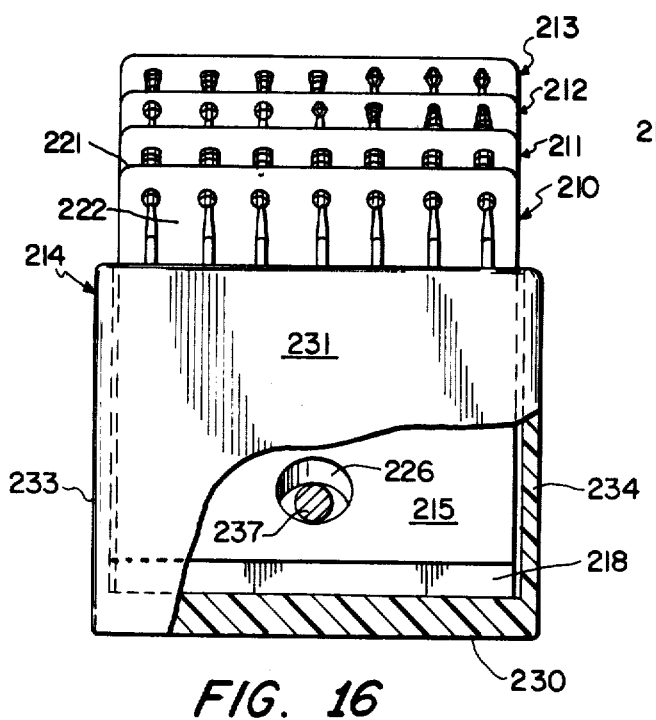

FIGS. 14–16 illustrate dental burr holders combined with a support in accordance with another embodiment of the invention. Here, four burr holders 210–213 are combined with a supporting receptacle 214. Except for their heights, holders 210–213 are identical and only holder 210, FIG. 14, will be described in detail. Holder 210 is in the form of an integral block of white or milky white polypropylene having mutually parallel flat front and back faces 215 and 216, respectively, a flat rectangular top face 217, a flat rectangular bottom face 218, flat mutually parallel end faces 219, 220 and a portion 221 which projects upwardly from top face 217 at the back of the holder, the flat rear face of portion 221 constituting an extension of back face 216. Front face 222 of portion 211 is at right angles to top face 217 and the juncture between faces 217 and 222 is filleted at 223. Seven burr-receiving apertures 225 are provided, spaced apart along a straight line parallel to front and back faces 215, 216. Each receptacle is in the form of a blind bore at right angles to and opening upward through top face 217, each bore 225 being provided with a short frustoconical guide surface 225a to aid in insertion of the burr shank into the bore. As will be clear from FIGS. 15 and 16, the length of bores 225 is such that when a burr is inserted in the bore, with the end of the shank engaged with the bottom of the bore, the burr tip is disposed below the top edge of portion 221. The holder is completed by a right cylindrical through bore 226 extending at right angles to an opening through faces 215, 216 in a position centered between end faces 219, 220 and adjacent bottom face 218.

As will be clear from FIGS. 15 and 16, holders 210≧213 are of differing heights, the heights progressing from holder 210 to holder 213. The height of portion 221 for all of burrs 210–213 is the same, the increase being in the distance between bottom wall 218 and top wall 217. However, the distance from bottom wall 218 to through bore 226 is the same for all of holders 210–213.

Support 214 is an open top receptacle molded as an integral piece from the same white or milky white polypropylene used for holders 210–213. Support 214 comprises a flat bottom wall 230 of rectangular plan configuration, flat rectangular front and back walls 231 and 232, respectively, and flat rectangular end walls 233, 234. The upper edges of walls 231–234 lie in a common plane parallel to the bottom face of bottom wall 230. Front and back walls 231, 232 are provided respectively with coaxially aligned circular openings 235 and 236 to snugly embrace the respective end portions of a retaining pin 237 which has a knurled head 238 exposed behind wall 232 so that the retaining pin can be easily inserted and removed. Openings 235, 236 are coaxial along a line parallel to bottom wall 230 and spaced above the upper surface of that wall by a distance equal to the vertical space between bottom face 218 and the axis of bore 236 in holders 210–213. The diameter of pin 237 is small as compared to the diameter of through bores 226.

With pin 237 removed, holders 210–213 are inserted, bottom face 218 down, into support 214 and the group of holders is held in upright position, with faces 218 in flush engagement with bottom wall 230. Retaining pin 237 is then installed, with the pin passing through the bores 226 of all of the holders 210–213 and being retained by a friction fit with openings 235, 236. As a group, holders 210–213 are then pivoted rearwardly, each holder rocking about the corner between bottom face 218 and back face 216, until the back face of holder 213 reset upon the upper edge of back wall 232 of support 214 and the four burr holders are engaged back wall-to-front wall in the manner shown in FIG. 15. From FIG. 16, it will be seen that the space between end walls 219 and 220 of the holders 210–213 is slightly less than the space between end walls 233, 234 of the support, so that insertion of the burr holders downwardly into the support and pivoting of the burr holders is freely allowed.

When holders 210–213 are positioned as seen in FIG. 15, portion 221 of each of holders 210–212 projects rearwardly and upwardly significantly beyond the front edge of top wall 217 of the next adjacent holder but the upper edge of portion 221 is below the location occupied by the tips of the burrs held by the next adjacent holder. Top faces 217 of the holders lie in progressively higher locations, progressing from front to back, so that the upper portions of the burr holders are disposed in staircase relation. Further, since the burr holders are inclined rearwardly, top faces 217 now slant downwardly and rearwardly, so that the angular dispositions of faces 217 and 222 are substantially the same (relative to a horizontal surface on which support 214 rests) as described with reference to the embodiment of FIGS. 6–8. When a burr is to be selected from holder 210, selection is made with all of the holders in the positions seen in solid lines in FIG. 15. When the selection is to be made from holder 211, holder 210 is pivoted forwardly against front wall 231 of support 214 before the selection is made. If the selection is to be made from holder 212, both holders 210 and 211 are pivoted forwardly before the selection is made. If the selection is to be made from holder 213, all of holders 210–212 are first pivoted forwardly.

Figure 18:
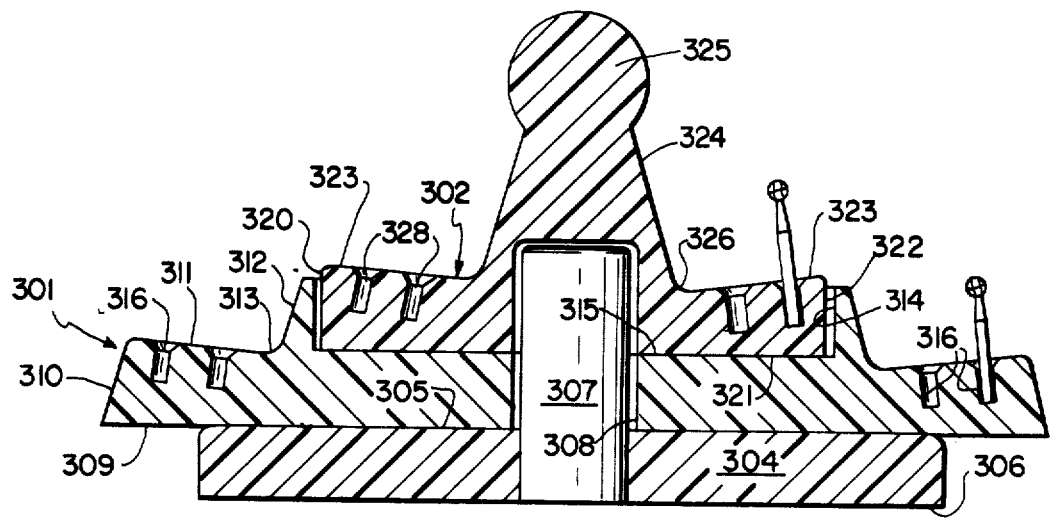
FIG. 18 is a vertical sectional view taken generally on line 18—18, FIG. 17.
Figure 17:
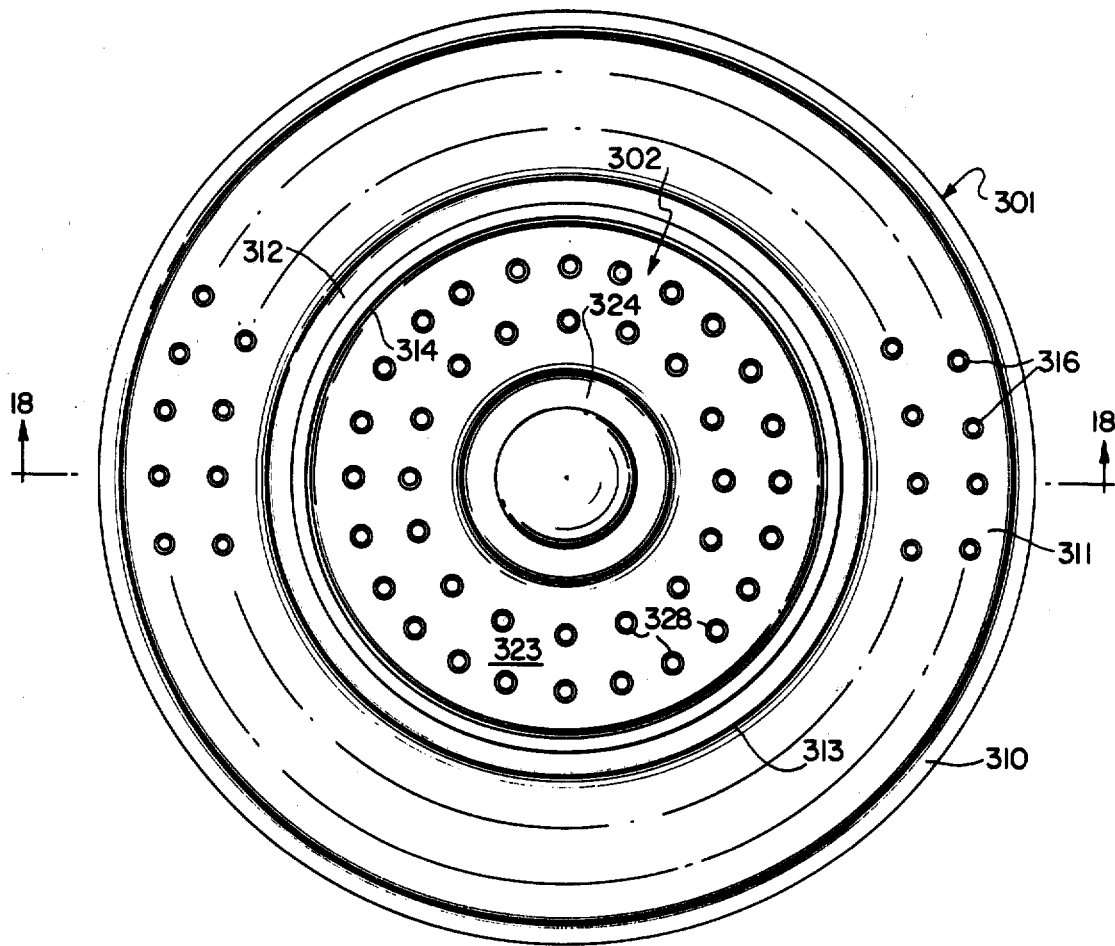
FIG. 17 is a top plan view of another embodiment.

When larger quantities of dental burrs are to be held and displayed, the embodiment of the invention shown in FIGS. 17 and 18 can be employed. In this embodiment, two circular burr holders 301 and 302 are carried by a support 303 for free independent rotation of both holders about a vertical central axis. Support 303, FIG. 18, comprises a base 304 which is of circular top plan and has flat top and bottom faces 305 and 306, respectively. At its center, base 301 carries an upright trunnion pin 307 presenting a right cylindrical surface. Holder 301 is an integral piece of circular top plan shape and having a central bearing opening 308 through which pin 307 extends, the flat bottom face 309 of the holder resting in flush sliding contact on top face 305 of base 304. The peripheral surface 310 of holder 301 is frustoconical, tapering upwardly and inwardly at a small angle of, e.g., 15°. The top of holder 301 includes a surface portion 311 which is annular and tapers downwardly and inwardly at an angle of from about 5° to about 10°, the inner periphery of surface portion 311 joining an upwardly and inwardly tapering frustoconical surface portion 312 in a smoothly curving fillet at 313. Surface portion 312 tapers at an angle of from about 95° to about 105° relative to the horizontal. Inwardly of surface portion 312, holder 301 has a circular upwardly opening recess which is centered on bearing opening 308 and is defined by a right cylindrical side wall 314 and a flat bottom wall 315. Holder 301 is provided with two circular series of circumferentially spaced bores 316, the bores being at right angles to and opening upwardly through surface portion 311, the two circular series being concentric with the rotational axis defined by pin 307 and opening 308, one series being spaced radially from the other.

Holder 302 includes a circular base portion 320 defined by a flat circular bottom surface 321, a right cylindrical outer surface 322, and an annular top surface portion 323, the latter tapering downwardly and inwardly at the same angle as surface portion 311 of holder 301. Base portion 320 of holder 302 is disposed in the recess defined by surfaces 314, 315 of holder 301, surface 314 loosely embracing surface 322, surface 321 being in flush contact with surface 315. At its inner periphery, top surface portion 323 joins the upwardly and inwardly tapering frustoconical surface 324 presented by a center post 325, there being a smoothly curving fillet 32 at the junction between the two surfaces. The holder has a bearing recess 327 which opens downwardly through surface 321 to form a continuation of bearing opening 308 and accommodate the upper end portion of pin 307. Holder 302 is provided with two circumferentially spaced series of bores 328 which are at right angles to and open upwardly through top surface portion 323, the two series being spaced apart from each other radially and concentric with the axis of rotation determined by pin 307.

Bores 316 and 328 are blind bores of such depth that, when the shank of a dental burr is inserted in one of bores 316, the tip of the burr will be located below the upper end of surface 312 and, when a burr is disposed in one of bores 328, the tip of the burr will be below the upper end of frustoconical surface 324. Accordingly, burrs retained by bores 316 are viewed against the visually uninterrupted background surface presented by surface portion 311, fillet 313, and frustoconical surface 312, while burrs retained by bores 328 are viewed against the visually uninterrupted background surface afforded by the combination of surface portion 323, fillet 326 and frustoconical surface 324. With holders 301 and 302 each made as an integral piece of white or milky white polypropylene, these background surfaces are markedly color contrasting with respect to the dark metal burrs.

Figure 19:
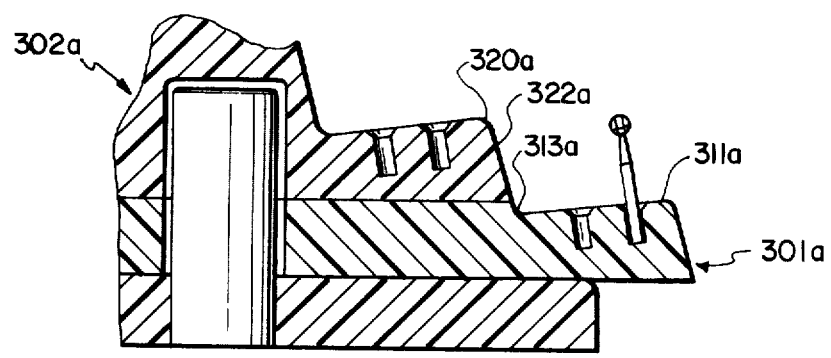
FIG. 19 is a fragmentary sectional view showing a modification of the device of FIGS. 17 and 18.

The upstanding circular portion defined by surfaces 312 and 314, FIG. 18, can be eliminated in the fashion shown in FIG. 19. Here, base portion 320a of holder member 302a presents a frustoconical outer surface 322a which tapers upwardly and inwardly. The lower edge of surface 322a is of such dimension as to constitute a continuation of fillet 313a, so that surface 311a and filet 313a of holder body 301a combine with surface 322a of holder body 302a to provide the visually uninterrupted color contrasting background against which the dental burrs held by body 301a are viewed.

While various embodiments have been chosen to illustrate the invention, it will be understood by those skilled in the art that various changes and modifications can be made therein without departing from the scope of the invention as defined in the appended claims.

What is claimed is:

1. A dental burr holder comprising, in combination:
    a holder body adapted to rest on a support and having a smooth upper surface interrupted only by a plurality of upwardly opening burr receiving apertures; and
    a member rigidly coupled to and projecting generally upwardly from said holder body without a space in between and having a smooth front surface which faces across said upper surface of said holder body,
    said upper surface and said front surface forming a background which color contrasts with the color of the burrs received in the apertures, and against which the burrs are viewed,
    said background being continuously color contrasting and substantially visually uninterrupted except for said burr receiving apertures to allow quick and accurate selection of the desired burrs adapted to be received in the holder and silhouetted against said contrasting background,
    said upper surface of the holder body forming an acute angle with a horizontal plane from 0° to about 10°.

2. A dental burr holder according to claim 1, wherein said holder body upper surface is planar.

3. A dental burr holder according to claim 1, wherein said front surface of the upwardly projecting member is planar.

4. A dental burr holder according to claim 1, wherein said upper surface of the holder body is white, and said front surface of the upwardly projecting member is white.

5. A dental burr holder according to claim 1, wherein said front surface of the upwardly projecting member slants upwardly and away from said upper surface of the holder body at an angle of from about 95° to about 105°.

6. A dental burr holder according to claim 1, wherein said upper surface of the holder body is white, and said front surface of the upwardly projecting member is off-white.

7. A dental burr holder according to claim 1, wherein the holder body and the upwardly projecting member are portions of an integral body of polymeric material;
    the holder body is hollow and defined by
    a top wall of generally rectangular plan configuration, and
    front, back and end walls depending from the top wall,
    the lower edges of the front, back and end walls lying in a common plane whereby the lower edges of the front, back and end walls can be engaged with a flat surface to support the holder on the flat surface.

8. A dental burr holder according to claim 7, wherein the holder body further comprises
    a plurality of internal portions depending from and integral with the top wall,
    the upwardly opening apertures being blind bores formed in said internal depending portions,
    the common plane of the lower edges of the front, back and end walls being spaced below said internal depending portions.

9. A dental burr holder according to claim 7, wherein the back wall of the body portion constitutes an extension of the upwardly projecting member.

10. A dental burr holder according to claim 8, wherein
    the internal depending portions are bosses and each of the upwardly opening apertures is formed in a different one of the bosses.

11. A dental burr holder according to claim 8, wherein
    there is a downwardly opening space between the depending internal portions and one of the depending walls of the body portion;
    the holder further comprising
    a metal weight member disposed in the downwardly opening space and releasably retained between said one depending wall and the adjacent depending internal portions.

12. A dental burr holder according to claim 11, wherein
    the plan configuration of the top wall of the holder body is an elongated rectangle and the front wall constitutes said one depending wall and depends from one of the long sides of the rectangle; and
    the metal weight member is a rod.

13. A dental burr holder according to claim 12, wherein
    the inner face of the front wall and the adjacent depending internal portions are provided with opposed indentations coacting with the rod to retain the same.

14. A dental burr holder according to claim 13, wherein
    the depending internal portions are bosses formed integrally with the top wall and spaced from each other in a rectangular plan, a plurality of the bosses being spaced along a line parallel to and adjacent to the front wall to constitute the adjacent depending internal portions,
    each of the upwardly opening apertures being formed in a different one of the bosses.

15. A dental burr holder according to claim 7, wherein
    the upwardly opening apertures are bores through the top wall of the holder body and are open at both ends;
    the dental burr holder further comprising
    means disposed within the hollow body and spaced below the top wall to support dental burrs extending downwardly through the bores.

16. A dental burr holder according to claim 1, wherein
    the holder body is of circular plan configuration,
    said smooth upper surface being an annular surface and the upwardly opening apertures being circularly spaced to provide at least one circular series of apertures concentric with the circular plan of the holder body;
    the upwardly projecting member is of circular transverse cross section and is located at the center of the holder body.

17. A dental burr holder according to claim 16, wherein
    the upwardly projecting member has a frustoconical outer surface which tapers upwardly and inwardly, the base of the frustoconical outer surface joining the inner periphery of the annular surface.

18. A dental burr holder according to claim 16, wherein
the annular surface of the holder body slants downwardly and inwardly.

19. A dental burr holder according to claim 16 and further comprising
means supporting the holder body for rotation about a vertical axis passing through the center of the body.

20. A dental burr holder according to claim 19, wherein
the means supporting the holder body comprises
a base adapted to rest on a horizontal support, and
a bearing pin projecting upwardly from the base,
the holder body having a downwardly opening bearing recess in which the bearing pin is engaged.

21. A dental burr holder according to claim 20 and further comprising
a second holder body of circular plan configuration disposed between the base and the first-mentioned holder body and having a central opening through which the bearing pin passes,
the second holder body being of larger diameter than the first-mentioned holder body and having a smooth annular upper surface portion which is visually interrupted only by a plurality of upwardly opening burr-receiving apertures,
said annular upper surface of the second body being located outwardly of and concentric with the first-mentioned holder body so as to be upwardly exposed.

22. A dental burr holder according to claim 21, wherein
the first-mentioned holder body has a flat bottom surface;
the second holder body has a flat upper surface; and
the first-mentioned holder body is supported on the second holder body with the flat bottom surface of the first-mentioned holder body engaging the flat upper surface of the second holder body,
the upwardly projecting member of the first holder body constituting means by which the two holder bodies can be rotated manually.

23. A dental burr holder according to claim 22, wherein
the flat upper surface of the second holder body is circular and forms the bottom wall of an upwardly opening recess in which the first-mentioned holder body is seated.

24. A dental burr holder according to claim 23, wherein
said upwardly opening recess is further defined by an annular wall portion projecting upwardly from the second body member and having a frustoconical outer surface which tapers upwardly and inwardly, the base of the outer surface of the annular wall portion joining the inner periphery of the annular upper surface portion of the second holder body.

25. In a dental burr holder, the combination of
a plurality of holder units each having
a smooth upper surface interrupted only by a plurality of upwardly opening burr-receiving apertures, and
an upwardly projecting portion rigidly coupled to said upper surface without a space in between and having a smooth front surface which faces across the upper surface,
the upper and front surfaces combining to present a background against which the burrs are viewed, which is visually substantially uninterrupted except by the burr-receiving apertures and which is continuously color contrasted with the burrs to be received in the apertures and silhouetted against said contrasting background,
said upper surface forming an acute angle with a horizontal plane of from 0° to about 10°; and
support means releasably supporting the holder units one behind the other in staircase relation,
the upwardly projecting portion of each holder unit extending upwardly beyond the upper surface of the one of the holder units immediately therebehind but being spaced below the upper limit of the front face of the upwardly projecting portion of said one holder unit.

26. The combination defined in claim 25, wherein
the support means includes a plurality of horizontal support surfaces which are disposed at successively higher levels progressing from the front to the back of the support means; and
the holder units are disposed each on a different one of the horizontal support surfaces.

27. The combination defined in claim 25, wherein
the support means comprises an open top receptacle having an upright rear wall and two mutually parallel end walls extending forwardly from the rear wall;
the holder units are disposed between the end walls and capable of being inclined rearwardly as a group, with the rearmost holder unit then supported by the rear wall of the receptacle and the remaining holder units being in turn supported by the rearmost holder unit.

28. The combination defined in claim 27, wherein
each of the holder units has an opening which extends through the holder unit from front to back near the bottom of the holder unit; and
the support means further comprises
an elongated retaining member extending through all of said openings,
the transverse dimension of the retaining member being small in comparison to the transverse dimension of said openings, whereby the holder units are free to pivot relative to the retaining member.

29. A dental burr holder comprising, in combination:
a holder body adapted to rest on a support and having a smooth upper surface interrupted only by a plurality of upwardly opening burr receiving apertures; and
a member rigidly coupled to and projecting generally upwardly from said holder body without a space in between and having a smooth front surface which faces across said upper surface of said holder body,
said upper surface and said front surface forming a background which color contrasts with the color of the burrs received in the apertures, and against which the burrs are viewed,
said background being continuously color contrasting and substantially visually uninterrupted except for said burr receiving apertures to allow quick and accurate selection of the desired burrs adapted to be received in the holder and silhouetted against said contrasting background, said holder body upper surface and said upwardly projecting member front surface being planar and white, said upwardly projecting member front surface slanting upwardly and away from said holder body upper surface at an angle of from about 95° to about 105°, said holder body upper surface forming an acute angle with a horizontal plane of from 0° to about 10°.

* * * * *